(12) United States Patent
Hansen

(10) Patent No.: US 6,759,205 B2
(45) Date of Patent: Jul. 6, 2004

(54) **CONSTRUCTION OF A STRAIN OF *BACILLUS SUBTILIS* 168 THAT DISPLAYS THE SUBLANCIN LANTIBIOTIC ON THE SURFACE OF THE CELL**

(75) Inventor: J. Norman Hansen, Silver Springs, MD (US)

(73) Assignee: University of Maryland, College Park, MD (US)

( * ) Notice: Subject to any disclaimer, the term of this patent is extended or adjusted under 35 U.S.C. 154(b) by 313 days.

(21) Appl. No.: 09/893,600

(22) Filed: Jun. 29, 2001

(65) Prior Publication Data

US 2002/0019518 A1 Feb. 14, 2002

Related U.S. Application Data

(60) Provisional application No. 60/215,449, filed on Jun. 29, 2000.

(51) Int. Cl.$^7$ ............... C07K 14/195; C07K 19/00; G01N 33/53
(52) U.S. Cl. ............ 435/7.1; 435/7.32; 435/219; 530/350; 530/825
(58) Field of Search ................. 435/7.1, 7.32, 435/219; 530/350, 825, 388.4; 424/196.1

(56) References Cited

U.S. PATENT DOCUMENTS

| | | | |
|---|---|---|---|
| 5,218,101 A | 6/1993 | Hansen | 536/23.7 |
| 5,516,682 A | 5/1996 | Hansen | 435/252.3 |
| 5,576,420 A | 11/1996 | Hansen | 530/324 |
| 5,861,275 A | 1/1999 | Hansen | 435/69.1 |
| 5,885,811 A | 3/1999 | Hansen | 435/172.3 |
| 6,153,405 A | 11/2000 | Hansen | |

FOREIGN PATENT DOCUMENTS

WO  WO 00/39152  7/2000

OTHER PUBLICATIONS

J. Rudinger, Peptide Hormones (Ed. J.A. Parsons, Univ. Press; Jun. 1976) pp. 1–6.*
U.S. patent application Ser. No. 60/215,449, Hansen, filed Jun. 29, 2000.
Hansen, "Nisin and Related Antimicrobial Peptides", Biotechnology of Antibiotics, Second Edition, pp. 437–467.

* cited by examiner

*Primary Examiner*—Bennett Celsa
(74) *Attorney, Agent, or Firm*—Arent Fox PLLC

(57) ABSTRACT

A sublancin peptide variant (lantibody) having a spacer region and a subtilin leader peptide fused to the C-terminal end of the mature sublancin peptide provide an anchoring means for inserting and retaining the lantibody in a host cell wall without affecting the intracellular processing of the lantibody, host cell expression of the molecule on the cell surface or the biological activity of the mature sublancin peptide in extracellular, cell-wall-bound form. Target molecules that bind to the lantibody and methods of engineering a peptide variant gene, plasmid and a host cell transformant are described as are methods of using a lantibody to identify new target molecules.

8 Claims, 8 Drawing Sheets

Sublamcin 168   Figure 1

```
AGAAGTGTCTCAGTCACGTTATCGAATATTGAGGATGATGTTAATCAGCAGCTGAGTTTATTTGAAGTGG
ATAATGAAAAGAGAAGGAAACTCGGTTTTGTAATGGATGGGATTACAACTAAATACGGCTCTAAAGCGAT
                                                      LPHF1--->
TCTGAGAGCAGTTTCTTATACACCAGCAGGAACTGCACTTCAACGAGCTGGATTAACAGGTGGGCATAAG
AGTTAAGATAAATTTAAACTTATATAACACATCGCTTAAAGTTTTTTTGTTTTAAAAACTTAAAAAACAT
                                   |---------> yolF ------->
GGTAAAATTATATAAAAACATAAGAAAGAGTGATTAT ATGGAATATGTAGTTATGATAATCATTTTATTA
GCACTTTTCTTTATTTTTACTGTTTTCCTAAATACACGTTATAGTTTTGATGAAAAATGCTTAGTCTTAA
AATTTGGTTTATCTAAAACAGAAATTCCAATTAATCAAATAGTTAGTATTAAAGAGTCAGACAAGTATGG
AGTTGCAGATAATATCGATTATAAAATTGGTATGCCATATGCTCAACCAGATAGAATTGTTATTGAAACT
                                          <------- yolF <---------
ACAAATAAGCGTTTTCTAGTTTTTTTAAATGGAGCTCAACAATTTATTCAAAAGTATAAAAGGGTTAGTG
--|
TT TGAACATAAAAAAGTACCTTCTTACAATAGAAGGTACTTTTTTGTATCTATAATTATTAAAAATTTAC
CTAAATTTTTATCATTATTAATTCAAAATAAATCCATAATAGTCAATTTTATTTAGTGTATTACAACCAA
                                          <---LPHR1, (LPHF2, LPVF2-->)
TTCTGTTTATTGATAGGTAATAAAGTTTTTTTTCTATGATTTATGAACAAGTTTCCTTATAATTTTCAAA
             -35                      -10
AAAAAATAAAAAATATGGTTGAATTTAGATTTATCTTCCTTTATATTAAAAAATGTAATCCGGATTGCAA
      r.b.s.       |------> sunA leader region-------->
ACAAATGGGGAGGTTTTACAA ATGGAAAAGCTATTTAAAGAAGTTAAACTAGAGGAACTCGAAAACCAAA
              <---LPHR2           <---LPVR2     NLPVF3----->
    sunA mature region --------->
AAGGTAGT GGATTAGGAAAAGCTCAGTGTGCTGCGTTGTGGCTACAATGTGCTAGTGGCGGTACAATTGG
            <------ sunA <----------- Pst I |
TTGTGGTGGCGGAGCTGTTGCTTGTCAAAAC TATCGTCAATTCTGCAGA TAAAACATTTGTAGAGGGAAT
        LPVF4--->              LPHF3--->
                                         <----LPPMR2
                                |-----------> sunT -------->
ATTTTAAATATTCCCTCATATTTAAAGCGGGGATTGAAA TTGAATAAGAAAAAGAAATATGTTCATACTA
AACAGTTTAATAGTCATGATTGTGGACTAGCTTGTATCTCGTCAATTTTAAAGTTTCATAACCTTAACTA
TGGAATTGATTTCTTACTAGACCTAATTGGGGATAAGGAAGGCTATAGTTTAAGAGACTTAATTGTTATT
TTTAAGAAGATGGGGATAAAAACTAGGCCACTTGAATTGCAAGAAAATAAGACATTCGAAGCCCTAAAAC
AAATAAAGCTCCCTTGTATAGCTTTGTTAGAAGGGGAGGAATATGGACATTACATAACAATATACGAAAT
TAGAAATAACTATTTACTTGTTAGTGATCCTGATAAAGACAAAATAACTAAAATAAAAAAAGAGGATTTT
GAAAGTAAATTCACAAACTTTATATTAGAAATTGACAAAGAGTCAATTCCTGAAAAAGAAAAAGATCAAA
AAAAACATTCTTACTTTTTTAAGGACATACTTTTTAGAAATAAATTGATCGTTTTTGTGATTTTATTGAC
TTCCTTGTTCGTTGTGGGTCTTGCTGTAGCTGGGTCGTTTTATATAAAGTTTCTAGTTGACCT------>
      <---LPHR3 & LPVR4       ----------> sunT ---------------------->
```

Figure 3

```
                                                                    EcoRI
                            pTZ sequence    <----------GAATTCCGGCTCTAAAGCGAT
TCTGAGAGCAGTTTCTTATACACCAGCAGGAACTGCACTTCAACGAGCTGGATTAACAGGTGGGCATAAG
AGTTAAGATAAATTTAAACTTATATAACACATCGCTTAAAGTTTTTTTGTTTTAAAAACTTAAAAAACAT
GGTAAAATTATATAAAAACATAAGAAAGAGTGATTATATGGAATATGTAGTTATGATAATCATTTTATTA
GCACTTTTCTTTATTTTTACTGTTTTCCTAAATACACGTTATAGTTTTGATGAAAAATGCTTAGTCTTAA
AATTTGGTTTATCTAAAACAGAAATTCCAATTAATCAAATAGTTAGTATTAAAGAGTCAGACAAGTATGG
AGTTGCAGATAATATCGATTATAAAATTGGTATGCCATATGCTCAACCAGATAGAATTGTTATTGAAACT
ACAAATAAGCGTTTTCTAGTTTTTTTAAATGGAGCTCAACAATTTATTCAAAAGTATAAAAGGGTTAGTG
TTTGAACATAAAAAAGTACCTTCTTACAATAGAAGGTACTTTTTTGTATCTATAATTATTAAAAATTTAC
CTAAATTTTTATCATTATTAATTCAAAATAAATCCATAATAGTCAATTTTATTTAGTGTATTACAACCAA
    Bam HI  (   -900 bp   )  Bam HI
TTC GGATCC <----cat-----> GGATTCGTGTATTACAACCAATTC TGTTTATTGATAGGTAATAAA
GTTTTTTTTCTATGATTTATGAACAAGTTTCCTTATAATTTTCAAA
AAAAAATAAAAAATATGGTTGAATTTAGATTTATCTTCCTTTATATTAAAAAATGTAATCCGGATTGCAA
                            | Sublancin leader ----->    Xho I
ACAAATGGGGAGGTTTTACAA ATGGAAAAGCTATTTAAAGAAGTTAAACTCGAGGAACTCGAAAACCAAA
        | Sun A ------------>
AAGGTAGT GGATTAGGAAAAGCTCAGTGTGCTGCGTTGTGGCTACAATGTGCTAGTGGCGGTACAATTGG
                                                          Pst I  |
TTGTGGTGGCGGAGCTGTTGCTTGTCAAAACTATCGTCAATTCTGCAGA TAAAACATTTGTAGAGGGAAT ATTTTAAATATTCCCTCATATTTAAAGCGGGGATTGAAATTGAATAAGAAAAAGAAATATGTTCATACTA
AACAGTTTAATAGTCATGATTGTGGACTAGCTTGTATCTCGTCAATTTTAAAGTTTCATAACCTTAACTA
TGGAATTGATTTCTTACTAGACCTAATTGGGGATAAGGAAGGCTATAGTTTAAGAGACTTAATTGTTATT
TTTAAGAAGATGGGGATAAAAACTAGGCCACTTGAATTGCAAGAAAATAAGACATTCGAAGCCCTAAAAC
AAATAAAGCTCCCTTGTATAGCTTTGTTAGAAGGGGAGGAATATGGACATTACATAACAATATACGAAAT
TAGAAATAACTATTTACTTGTTAGTGATCCTGATAAACACAAAATAACTAAAATAAAAAAGAGGATTTT
GAAAGTAAATTCACAAACTTTATATTAGAAATTGACAAAGAGTCAATTCCTGAAAAAGAAAAAGATCAAA
AAAAACATTCTTACTTTTTAAGGACATACTTTTTAGAAATAAATTGATCGTTTTGTGATTTTATTGAC
TTCCTTGTTCGTTGTGGGTCTTGCTGAAGCTT--------->pTZ sequence
                 HindIII
```

Figure 4

```
                                              Sublancin leader→
←——— pLPcat
TTGCAAACAAATGGGGAGGTTTTACAA ATGGAAAAGCTATTTAAAGAAG
                                              MetGluLysleuPheLysGluV XhoI                                   sublancin prep-
TTAAACTCGAGGAACTCGAAAACCAAAAAGGTAGT GGATTAGGAAAAGC
AlLysLeuGluGluLeuGluAsnGluLysGlySer GlyLeuGlyLysAl tide→
TCAGTGTGCTGCGTTGTGGCTACAATGTGCTAGTGGCGGTACAATTGGTT
aGlnCysAlaAlaLeuTrpLeuGlnCysAlaSerGlyGlyThrIleGlyC KasI                                         Poly-
GTGGTGGCGGCGCCGTTGCTTGTCAAAACTATCGTCAATTCTGTAGAGGT
ysGlyGlyGlyAlaValAlaCysGlnAsnTyrArgGlnPheCysArgGly glycine20→                           BseRI
GGTGGTGGGGGAGGCGGGGGAGGGGGTGGTGGTGGAGGAGGTGGTGGTGG
GlyGlyGlyGlyGlyGlyGlyGlyGlyGlyGlyGlyGlyGlyGlyGlyGl subtilin leader→         XbaI
TGGTGGTATGTCAAAGTTCGATGATTTCGATCTAGATGTTGTGAAAGTCT
yGlyGlyMetSerLysPheAspAspPheAspLeuAspValValLysValS Stop    PstI
CTAAACAAGACTCAAAAATCACTCCGCAATAGAGTCCTGCAGATAAAACA
erLysGlnAspSerLysIleThrProGln  *
                                          pLPcat ———▷
```

Figure 7

CONSTRUCTION OF A STRAIN OF *BACILLUS SUBTILIS* 168 THAT DISPLAYS THE SUBLANCIN LANTIBIOTIC ON THE SURFACE OF THE CELL

This application claims priority under 35 U.S.C. §1.119 (e) to provisional application serial no. 60/215,449, filed Jun. 29, 2000.

This invention was made with Government support under Contract No. AI24454 awarded by the NIH.

FIELD OF THE INVENTION

This invention relates to the construction and expression of a sublancin-derived Lantibody Display Peptide in a strain of *Bacillus subtilis* and the use thereof.

BACKGROUND OF THE INVENTION

Lantibodies were initially described by the inventors of this application (1). Lantibodies are derived from lantibiotics which are a family of natural peptides that have antimicrobial activity. Lantibiotics have unique chemical and biological properties that are conferred by the presence of unusual amino acid residues such as dehydroalanine, dehydrobutyrine, lanthionine, and 3-methyllanthionine. The dehydro residues are electrophilic, and are capable of reacting with nucleophilic groups on polypeptide surfaces (1). By constructing suitable polypeptide environments around the dehydro residues, it is possible to control the reactivity and specificity of the dehydro residues, to react in a highly specific way with particular nucleophilic groups on the polypeptide surface. This reaction can alter the biological activity of the polypeptide surface, and if it is on a pathogen such as a bacterium or a virus, the activity of the pathogen can be destroyed. If the polypeptide surface is part of an enzyme, the activity of the enzyme can be altered in some useful way.

In this disclosure, a novel process by which the lantibodies are designed and constructed is described, and the lantibodies thus produced are versatile in their use. Also disclosed is a novel means for the identification of lantibodies which bind specifically to desired target molecules.

The inspiration for this invention is the mammalian immune system, in which stem cells differentiate into B-cells. This differentiation involves random recombination events among the variable regions of antibody genes, so that the resulting B-cell becomes programmed for the production of a particular antibody whose antigen-combining regions have been determined by a random process. The antibody that any B-cell can make is then displayed on the surface of the respective B-cell, and this surface antibody can interact with circulating pathogenic antigens. In the event that an antigen binds tightly to one of the displayed antibodies, the binding triggers cell division and further maturation of the B-cell into a plasma cell, which then produces and secretes large quantities of the antibody, which then leads to the destruction of the antigen (2–3).

Essential features of this natural process include the random generation of a population of antibodies, each of which is produced by a cell that displays the antibody that it is genetically programmed to make. Then, there is a highly-efficient process for the selection and amplification of those antibodies that bind to a specific antigen. The amplification is achieved by stimulating the division of those B-cells that display the antigen-binding antibodies.

Using discoveries in the Inventor's laboratory, the lantibody that a given bacterial cell produces is displayed on the surface of the cell. It is demonstrated that a population of lantibody producing cells can be exposed to a target molecule, and that the cells whose surface lantibodies can bind to the target can be specifically recovered, so that the population of target-binding cells is enriched. This enriched population can be subjected to repeated selection and enrichment, so that a purified population of the specific antigen-binding cells can be obtained. A very important aspect of this process is that once the target-binding cells are obtained, the lantibody that is displayed on the surface of the cell can be further characterized or the corresponding lantibody peptide can be used to identify novel nucleophilic groups on target molecules or even novel target molecules.

Knowledge of the structure of the lantibody is very important, because it can provide the basis of understanding the fundamental principles that are responsible for causing a particular lantibody to bind to a particular antigen. This knowledge can be applied to the rational design of new lantibodies that are directed toward nucleophilic targets, so that the methods by which new lantibodies are made is not solely dependent on random chance.

SUMMARY OF THE INVENTION

An object of the invention is a lantibiotic-spacer-subtilin leader sequence in anchoring a lantibiotic peptide to the cell surface of a host cell. The construction of the lantibiotic-spacer-subtilin chimera comprises lantibiotic structural regions being fused at the C-terminus to a spacer which is fused to the N-terminus of the subtilin signal leader sequence.

Another object of the invention is a mutagenesis-vector for replacing the endogenous lantibiotic chromosomal gene with a mutagenized lantibiotic sequence in an expression host.

Another object of the invention is a *Bacillus subtilis* host strain engineered to contain a deletion of a portion of the sun A gene with the remaining portion of the sunA gene being flanked by an erm gene.

Another object of the invention is a method for selecting a Lantibody Display Peptide having the ability to bind to a nucleophilic group on a target molecule.

Another object of the invention is a kit containing a bacterial host cell expressing a Lantibody Display Peptide for use in the identification of a target molecule.

BRIEF DESCRIPTION OF THE FIGURES

FIG. 3. Location of template regions for PCR primers used to synthesize fragments used in the construction of mutagenic vectors and host. *B. subtilis* 168 sequence surrounding the sublancin structural gene (sunA), which was used to construct mutagenic plasmids is shown. The locations of the template regions of the mutagenic PCR primers are underlined, and the complete sequences of the primers are shown in Table II. Each primer name is accompanied by an arrow that shows the direction of priming. Nucleotide sequences in bold are those that encode the YolF, SunA, and N-terminal end of the sunT ORFs, respectively. Gene sequences are from (4) and (5).

FIG. 4. Sequence of the EcoRI-HindIII insert of the pLPVc integrative plasmid used to delete and replace the natural sunA gene with a mutagenized sunA gene in the *B. subtilis* 168 chromosome. A chloramphenicol (cat) gene has been inserted at an engineered BamHI site to provide a selective marker. An XhoI site has been engineered into the sunA leader region by means of a silent mutation to facilitate the construction of structural mutants. The PstI site at the 3'-end of the sunA gene is a natural restriction site. The EcoRI-HindIII fragment is cloned into the EcoRI and HindIII sites of the pTZ mps (SEQ ID NO. 1).

FIG. 7. The sequence of sunA-PG$_{20}$-S$_L$ in pAV2. The reading frame of the sunA-PG$_{20}$-S$_L$ gene and the sequence of the peptide sequence the gene encodes are highlighted in bold (SEQ ID No. 2). Also highlighted are the restriction sites as well as the leader peptide, sublancin prepeptide, polyglycine, and subtilin leader coding regions of the gene. The sequences flanking the gene correspond to those of the mutagenesis cassette vector pLPcat.

DETAILED DESCRIPTION OF THE INVENTION

Figure 1:
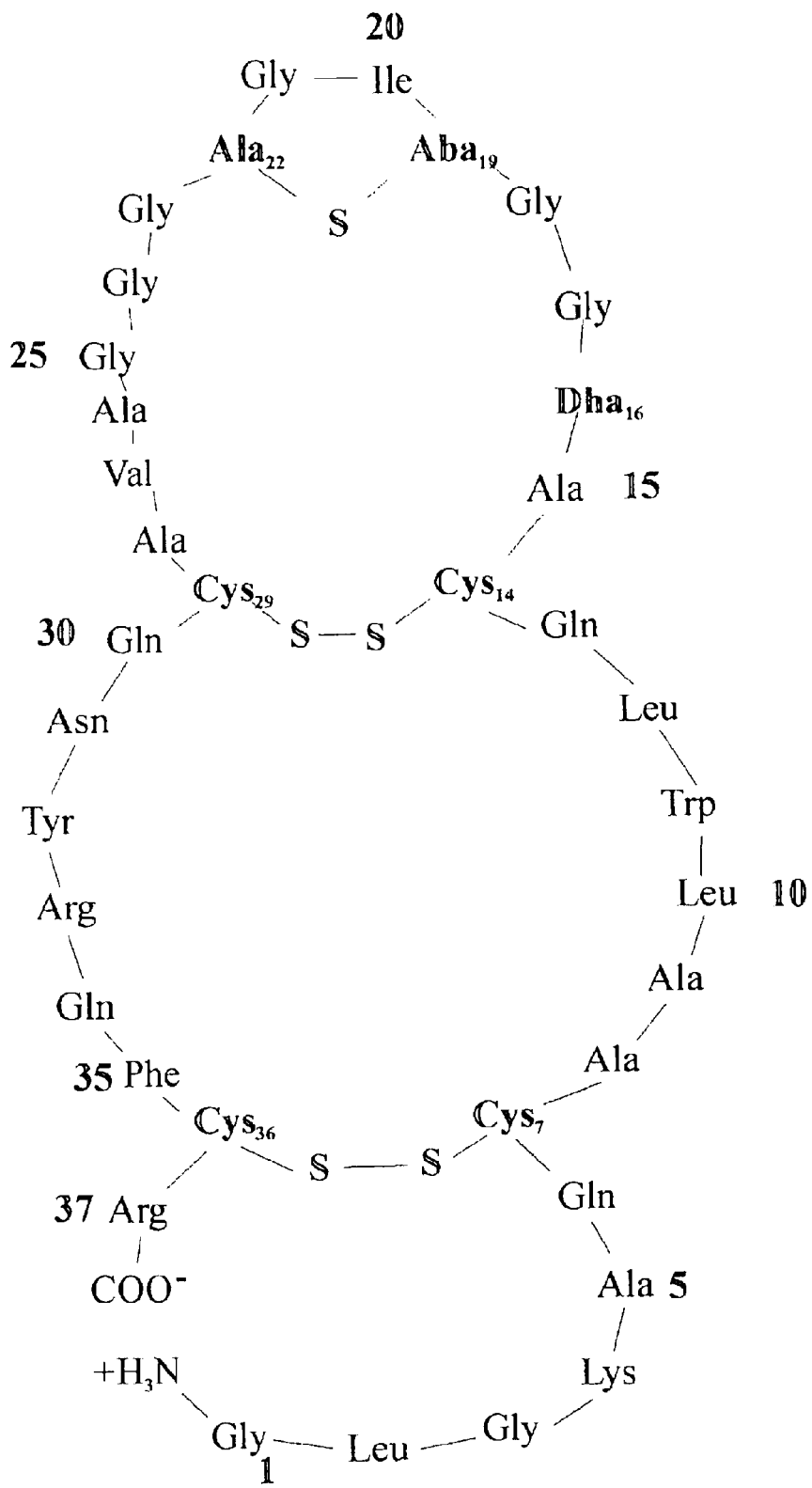
FIG. 1. Structure of sublancin 168.

The present invention explores the contribution of a spacer-subtilin leader peptide sequence in anchoring a lantibiotic peptide to the cell surface of a host cell. The construction of the lantibiotic-spacer-subtilin chimera comprises lantibiotic structural regions being fused at the C-terminus to a spacer which is fused to the N-terminus of the subtilin signal leader sequence. The inventors have discovered that the chimeras in which the C-terminal portion of the structural region correspond to the spacer-subtilin leader are processed so as to anchor the chimeric molecule to the surface of the host cell, and to give an active lantibiotic product.

The strategy for displaying the peptide is based on a discovery in the Inventor's laboratory while doing experiments with the lantibiotic called subtilin. A feature of all lantibiotics is that they are expressed as polypeptide precursors that contain a leader peptide that is cleaved at some stage during the biosynthetic process. In studies to determine the role of the subtilin leader peptide, it was demonstrated that the subtilin leader has a strong affinity for the cell wall of *B. subtilis* 168, and that a crucial step in subtilin biosynthesis is the proteolytic cleavage of the leader, which results in release of the subtilin into the medium. Without this cleavage, subtilin cannot be released (7).

This invention is based on the fact that incorporation of the subtilin leader segment into the lantibiotic peptide results in a form of lantibiotic that is retained in the cell wall instead of being released into the medium.

The term "gene" refers to a polynucleic acid or a nucleotide which encodes a peptide, a prepeptide, a protein or a marker, or to a vector or plasmid containing such a polynucleic acid or nucleotide.

A "chimera" refers to a fusion peptide or protein which is comprised of a part from a first peptide or protein, and a part from one or more additional proteins or peptides.

A "mutant" gene or peptide refers to a gene having a sequence in that one or more bases or residues are deleted, substituted or added at any position therein, including either terminus.

A "Lantibody Display Peptide" refers to a lantibiotic peptide sequence containing a C-terminal amino acid spacer-subtilin leader sequence, which allows for a chimeric peptide or protein product to be expressed on the surface of a host cell through the binding of the chimeric molecule to the cell surface by the subtilin leader peptide. Advantageously, the fusion molecule retains the functional characteristics with respect to the lantibiotic portion of the molecule.

In the present application, "biological activity" refers to activity against a preferably nucleophilic target molecule. Biological activity includes but is not limited to activity against or for modifying enzymatic activity of an enzyme, inhibiting proliferation or growth of an infectious particle or a cancer cell, or blocking the binding of a ligand to its receptor. Most preferably the activity is against *Bacillus cereus* spores and/or vegetative cells. Preferably, biological activity against *Bacillus cereus* spores is measured using the "halo assay" described in the experimental section hereunder.

The present invention concerns nucleotides, vectors and constructs encoded thereby, which encode a chimeric or mutant lantibiotic polypeptide of the formula:

(lantibiotic)-(spacer)-(subtilin leader peptide)

wherein the antibiotic is selected from the group consisting of nisin, subtilin, epidermin, pep5, epilancin, duramycin A, duramycin B, duramycin C, cinnamycin, ancovenin, meracidin, actagardine, lacticin 481, streptococcin AFF22, salivaricin A, lactocin S, carnocin IU 49, mutacin II, cytolysin, sublancin, and a mutant of any of the aforementioned lantibiotics. Preferably, the antibiotic retains its functional characteristics when expressed in a lantibiotic-producing host. More preferably the lantibiotic is sublancin, and most preferably, the sublancin is sublancin 168.

The present construct includes a peptide spacer comprising from 1 to 40 amino acids, the spacer being of sufficient length and design to produce a region with unstructured secondary conformation. In this regard, non-polar amino acids are preferred. The amino acid is preferably one or more amino acids selected from the group consisting of glycine (G or Gly), alanine (A or Ala), valine (V or Val), isoleucine (I or Ile) and leucine (L or Leu). Preferably the amino acid is glycine.

The present construct also includes a subtilin leader peptide shown as residues 58–81 of SEQ ID No. 2. The entire sequence is not necessary, however, it has been shown that residues 78–81 are necessary. Therefore, the subtilin leader peptide of the claimed construct can be residues 58–81, 68–81, 73–81 or 78–81 of SEQ ID No. 2.

"Sublancin 168" (sun A gene) is the preferred construction platform for the Lantibody Display Peptide. Sublancin 168 is a lantibiotic that was discovered in the laboratory of the Inventor, the structure of which is shown in FIG. 1.

Sublancin has many attributes that make it an ideal platform on which to construct the Lantibody Display Peptide Sublancin is a lantibiotic that is endogenous to the gram-positive bacterium *Bacillus subtilis* 168, which is a bacterial strain that has been intensely studied. The complete sequence of its genome is known, and excellent tools for genetic manipulation are available. Strain 168 has been widely used for industrial production of genetically-engineered biomaterials, so its use for the industrial production of sublancin 168 derivatives is straightforward. The natural level of sublancin 168 production by strain 168 is good (4), which facilitates efficient production of the derivatives.

Sublancin 168 is intrinsically highly stable, which enhances the stability of sublancin derivatives.

Sublancin contains several distinct structural regions, which are defined by the locations of the disulfide bridges. An important aspect is that residues 1–13 have a high propensity for α-helix formation, whereas residues 30–37 have a high propensity for β-sheet formation. In contrast, residues 5–28 are very rich in glycines, which tend to disrupt both α-helix and β-sheet, and possess little, if any secondary structure. Without being bound by scientific theory, it is believed that the 1–13 region of α-helix and the 30–37 region of β-sheet form stable secondary structures, and perhaps tertiary interactions with each other, and constitute a "constant" region, and this constant region is preferably unchanged within the Lantibody Display Peptide. It is the region consisting of residues 15–28, that contain the unusual residues of sublancin, that are preferably subjected to mutagenesis, as this region is conceptually the "variable" region of the lantibodies. It is in this way that the lantibody is conceptually based on the mammalian antibody. It is the variable region of the lantibody that corresponds to the antigen-combining region of the antibody, and the constant regions of the lantibody correspond to the constant, or "framework" regions of the antibody.

However, there are important fundamental differences between a lantibody and an antibody. Compared to antibodies, which are typically 150,000 Da, lantibodies are very small molecules having molecular weights less than 4,000 Da. This 40-fold difference in size allows lantibodies to gain ready access to targets that are completely inaccessible by antibodies. Another fundamental difference is the presence of unusual residues in antibodies, which provide functionalities that antibodies cannot possess. For example, the dehydro residues are electrophilic, and can become covalently attached to specific nucleophilic targets.

Figure 2:
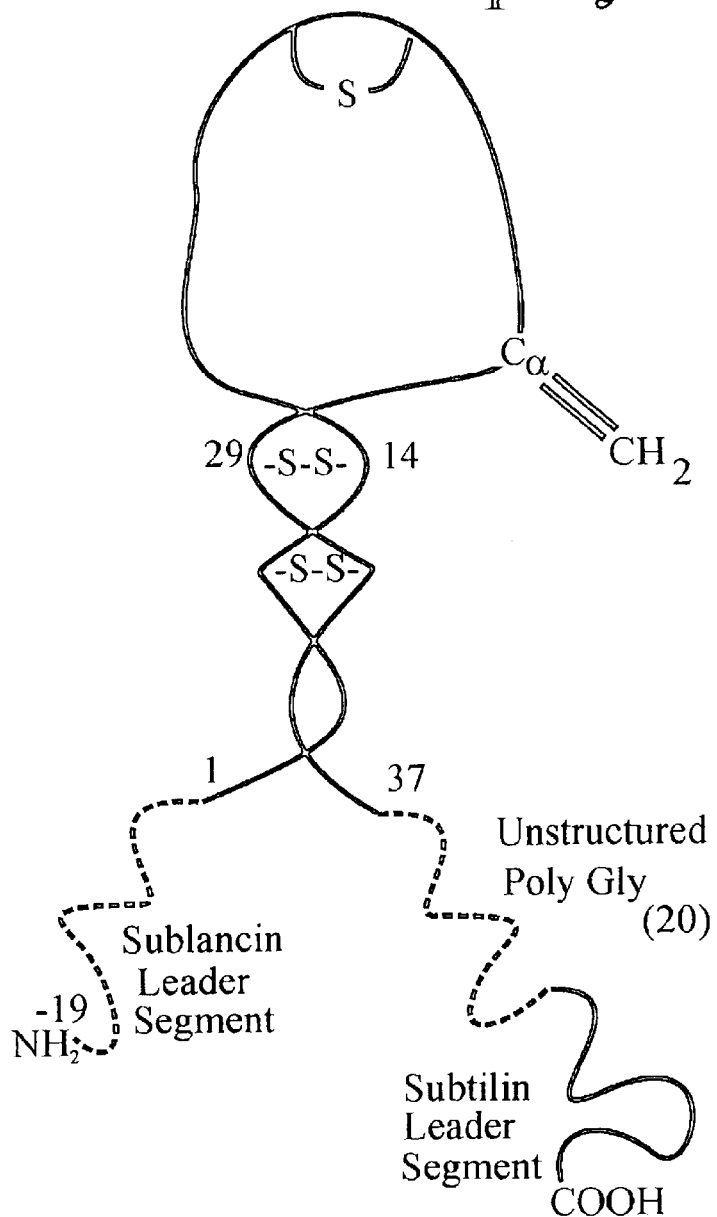
FIG. 2. Structure of sublancin Lantibody Display Peptide.

FIG. 2 shows how the sublancin prepeptide has been modified to become a Sublancin Display Peptide. It retains the normal sublancin leader sequence at the N-terminal end, which supports the normal functions of posttranslational modifications, translocation through the membrane, and cleaving away in its normal fashion.

For the peptide to be displayed on the surface of the cell, a spacer has been fused to the C-terminus of the lantiobiotic peptide followed by the subtilin leader sequence. The secondary structure of the chimeric molecule is disrupted by the introduction of the spacer into this region of the molecule, allowing the molecule to extend in an upward direction. The spacer can contain from 1–40 residues, preferably, 10–30 residues, more preferably from 15–25, and most preferably about 20.

A proviso for the subtilin leader segment is that it retain its affinity for the cell wall. The subtilin leader is preferably attached through its N-terminal end to the spacer, therefore it is not subject to cleavage by the signal peptidase. On a wild-type subtilin preprotein, the leader sequence is normally cleaved at its C-terminal end, thus generating the mature subtilin protein.

The complete subtilin leader segment is 24 residues long (8), and this together with a 20-residue spacer places 44 residues at the C-terminus of the lantibiotic peptide. In a preferred embodiment, the chimeric sublancin Lantibody Display Peptide comprises the formula:

sunA-PG$_{20}$-S$_{L1-24}$

In a preferred embodiment, a sublancin-derived Lantibody Display Peptide is generated by transfecting a B. subtilis 168 ermΔSun host cell with a linearized mutagenesis plasmid pAV2 containing the sequence of sunA-PG$_{20}$-S$_L$. The pAV2 vector is depicted in FIG. 7. The transformed host is then cultured in medium to allow the Lantibody Display Peptide to be expressed.

Preferably, the bacterial host transformed with the inventive mutagenesis vector is a sublancin-producing host. More preferably, the sublancin producing host is a strain of Bacillus subtilis such as B. subtilis 168. Most preferably, the host is B. subtilis LPeΔsunA.

When the gene for this peptide is expressed in B. subtilis 168, the expected sequence of events is as follows. The gene is transcribed, translated and posttranscriptionally-modified to give the precursor peptide in FIG. 2. The precursor peptide is then secreted across the cytoplasmic membrane by means of sublancin leader segment which is recognized by the normal sublancin transporter system. Once in the cell wall, the sublancin leader is cleaved in the usual manner. Whereas sublancin itself would normally diffuse toward the surface and be released, the presence of the subtilin leader segment at the C-terminal causes the entire molecule to be retained within or on the cell wall.

Any suitable growth media can be used to culture the lantibody expressing cells, e.g., media comprising nitrogen sources such as yeast extracts, soy tripticase, peptone, salts, metal ions, citric acid, buffers, carbohydrates such as glucose, glycerol, lactose, sucrose, molasses, chalk, phosphates, ammonium sulfate and oil.

The variable region of a wild-type lantibiotic gene, or preferably a sublancin gene, can be mutagenized by any art-recognized methods and subcloned into the mutagenesis vector for transfection and stable integration through homologous recombination of the mutagenized gene into the chromosome of a susceptible host cell. A sublancin mutant that can be expressed and secreted by B. subtilis 168 is an object of this invention. The production of a mutated, mature sublancin protein is demonstrated hereunder.

Strategies are readily available to collect lantibody-expressing cells in order to obtain and characterize the lantibody that is responsible for binding to any given target molecule. Lantibody expressing cells which bind to a target molecule can be detected and purified by reacting the cells with an anti-sublancin antibody or an anti-target antibody followed by passage of the cells over any recognized methods for separating and enriching viable cells such as an immunoadsorption column, magnetic bead separation or flow cytometry. Following purification, the enriched cells are eluted and collected for analysis. The structure of the lantibody can be determined by sequencing the protein or polypeptide, or the gene that encodes it.

The lantibody protein or polypeptide or a mutant thereof, can be sequenced as follows: the proteins are reduced and alkylated in preparation for protease digestion. 75 μl 50 mM dithiothreitol (DTT) and 150 μl 100 mM iodoacetamide, both in 0.2 Na M borate, pH 8.0, are added to 100 μg lyophilized peptide and incubated overnight at room temperature in the dark. 1 ml 0.1% acetic acid, 0.01% trifluoroacetic acid (TFA) are added and the mixture immediately purified by HPLC as previously described (4), and fractions collected. The fractions containing alkylated peptide, as determined by subjecting 0.5 μl of each to matrix assisted laser desorption/ionization-time of flight MS (MALDI-TOF MS), are lyophilized and resuspended in 100 µl 100 mM NH$_4$CO$_3$, 1 mM CaCl$_2$, pH 8.0. Sequencing-grade trypsin (Sigma, St. Louis, Mo.) is added at a 1:50 enzyme to substrate ratio and the mixture incubated at 37° C. for 4 hours. 1 ml of 0.1% acetic aced, 0.01% trifluoroacetic acid (TFA) is added and the mixture immediately purified by HPLC as above, except the first step of the elution profile is 15% B over 5 minutes and the second step is from 15 to 65% B over 20 minutes. The fractions containing peptide fragments, as determined by subjecting 0.5 µl of each to MALDI-TOF MS, are lyophilized and resuspended in 25 µl 0.1% acetic acid, 0.01% TFA and sequenced using nanoESI-MS/MS.

The gene encoding the lantibody can be sequenced by any variety of art-recognized methods (6).

A population of surface-displayed lantibodies can be challenged by a biologically relevant target molecule of interest, which is preferably a nucleophilic group within a polypeptide sequence. Cells which bind to the target are those which synthesize a Lantibody having the ability to bind to the target.

Nucleophilic target molecules that bind to the lantibody include but are not limited to nucleophilic groups located on antigens, virus particles, bacterial cells, more preferably gram-positive bacterial cells, bacterial spores, vegetative bacterial cells, and the proteins and polypeptides on any of the aforementioned biologically relevant molecules including enzymes and receptors. Preferably, the target molecule has a nucleophilic group within a polypeptide chain. A nucleophilic group can also be located on a polypeptide surface where the polypeptide is in the form of a tertiary or quarternary complex.

An antigen being attached to a lantibody would be partially or completely blocked from interacting with its cognate binding partner. A binding partner may be an antibody or a receptor in either soluble or membrane-associated form.

Bacterial cells including but not limited to *Bacillus cereus* T. *Bacillus megaterium*, *Bacillus subtilis*, *Staphylococcus aureus* or *Streptococcus pyogenes*, would be killed or growth inhibited by an attached lantibody.

In accordance with the present invention, a lantibody attached to a spore would prevent spore outgrowth.

A virus particle that had its receptor binding sites blocked by a lantibody would preferably be rendered permanently non-infectious.

An enzyme that had its catalytic site blocked by an attached antibody would preferably be completely or partially inactivated. Alternatively, a lantibody may become attached to a regulatory site on an enzyme, whereupon its activity would be partially or permanently modulated according to the function of the regulatory site. Enzymes include but are not limited to proteases and protein kinases.

The display peptide was designed with the intention of allowing a functional antibody to be displayed on the outer surface of the cell wall. This object of the invention has been achieved by a series experiments some of which are described by way of the following non-limiting examples.

EXAMPLE 1

Construction of a Mutagenesis System to Create Mutations in the Sublancin Gene, and Introduction of the Mutations into the Chromosome The strategy that was developed for sublancin mutagenesis is the subject of a previous provisional patent application Ser. No. 60/215,449. It is similar to the strategy used for subtilin mutagenesis (9) which was to construct a host-vector pair with the vector being a plasmid used for the construction and propagation of the mutant gene, and the host being a *B. subtilis* 168 mutant with a deletion in the sublancin gene and an erm resistance marker. The plasmid vector was designed to contain homologies to the regions flanking the sublancin gene together with a cat selective marker, such that a double-recombination between the plasmid and the host results in replacement of the erm gene in the host with the mutagenized sublancin gene, together with the cat marker. After this recombination, the mutagenized sublancin gene is located precisely where the native gene had been, so that effects on expression would be minimized. Appropriate recombinants are identified by their loss of erythromycin resistance, and gain of chloramphenicol resistance.

Bacterial strains, cloning vectors, and culture conditions. Bacterial strains and cloning vectors are listed in Table I. Sublancin and its analogs were expressed and isolated as previously described (4). Competent *B. subtilis* 168 cells were prepared according to Young and Wilson (10).

TABLE I

| Bacterial Strains<br>Strain | Description | Source |
|---|---|---|
| BR151 | Wild type *Bacillus subtilis* 168 | BGSC[a] |
| *B. subtilis* LPeΔsunA | *Bacillus. subtilis* 168 in which the sublancin gene contains an in-frame deletion, and an erm selective marker | Invention |
| *B. subtilis* sunA' | Sublancin producer strain made by transforming pLPVc into *B. subtilis* LPeΔsunA | Invention |
| JM109 | Standard *E. coli* cloning strain | Life Tech.[b] |
| JM101 | Standard *E. coli* cloning strain | Life Tech.[b] |
| *B. cereus* T | Strain used to assay sublancin | BGSC |
| Cloning Vectors<br>Plasmid | Description | |
| pSUB8kb | An 8 kb fragment from *Bacillus subtilis* 168 containing the sublancin gene in pTZ18R | Ref[c] |
| pTZ18R | Standard cloning vector | USB[d] |
| pLPe□sunA | Plasmid used to construct *B. subtilis* LPeΔsunA | Invention |
| PLPc | Plasmid used to integrate a sublancin gene into the chromsome of *B. subtilis* LPeΔsunA | Invention |

Bacterial strains and plasmids used in this work.
[a]Bacillus Genetics Stock Center, University of Ohio, Columbus OH.
[b]Life Technologies, Gaitherburg MD.
[c](4).
[d]United States Biochemical Corp., Cleveland OH.

Cloning by PCR. The polymerase chain reaction (PCR) was used to generate the DNA fragments used for the construction of the plasmid vectors used for mutagenesis. Plasmid pSUB8kb was used as the template DNA for the PCR reactions. The sequences of the oligonucleotides used as primers in the PCR reactions are listed in Table II, and the template regions corresponding to these oligonucleotides are identified in FIG. 3. The reactions were performed using pfu DNA polymerase (Strategene, La Jolla, Calif.) during 30 cycles of denaturation at 95° C. for 30 sec, annealing at 50° C. for 90 sec, and extending at 72° C. for 3 min. The PCR fragments were cleaved with EcoRI and HindIII and cloned into the EcoRI-HindIII site of pTZ, which was propagated in *E. coli* JM101 or JM109. The PCR primers were designed in such a way that the plasmid constructs could be assembled by a sequence of ligation and cloning steps that added one PCR segment at a time, with each addition being confirmed by cloning and restriction analysis before adding the next segment. After the assembly was complete, the entire insert was subjected to dideoxy sequence analysis to confirm that it had been correctly assembled and that it contained no unintended mutations.

TABLE II

|  | Olionucleotide Sequence written 5' to 3' |
|---|---|
| LPHF1<br>SEQ ID No.3 | GACT<u>GAATTC</u>CGGCTCTAAAGCGATTC<br>    EcoRI |
| LPHR1<br>SEQ ID No. 4 | GGACT<u>AAGCTT</u> <u>GGATCC</u>GAATTGGTTGTAATACAC<br>    HindIII BamHI |
| LPHF2<br>SEQ ID No. 5 | GCAAC<u>GAATTC</u> <u>GGATCC</u>GTGTATTACAACCAATTC<br>    EcoRI   BamHI |
| LPHR2<br>SEQ ID No. 6 | TCGAA<u>AAGCTT</u> <u>GTTAAC</u>CTTTTCCATTTGTAAAACC<br>    HindIII HincII |
| LPHF3<br>SEQ ID No. 7 | TGGCA<u>GAATTC</u> <u>GTTAAC</u>TATCGTCAATTCTGC<br>    EcoRI   HincII |
| LPHR3<br>SEQ ID No. 8 | GGAGC<u>AAGCTT</u> CAGCAAGACCCACAACG<br>    HindIII |
| LPVF2<br>SEQ ID No. 9 | Same as LPHF2 |
| LPVR2<br>SEQ ID No. 10 | GGATG<u>AAGCTT</u> <u>CTCGAG</u>TTTAACTTCTTTA<br>    HindIII XhoI |
| NLPVF3<br>SEQ ID No. 11 | GTAG<u>GAATTC</u> <u>CTCGAG</u>GAACTCGAAAACC<br>   EcoRI   XhoI |
| LPPMR2<br>SEQ ID No. 12 | GGAGC<u>AAGCTT</u>TTAT<u>CTGCAG</u>AATTGACGATAG<br>    HindIII    PstI |
| LPVF4<br>SEQ ID No. 13 | GATT<u>GAATTC</u>GGCGCCGTTGCTTGTCAAAAC<br>    EcoRI |
| LPVR4<br>SEQ ID No. 14 | Same as LPHR3 |
| L13<br>SEQ ID No.15 | GTGTATTACAACCAATTCTG |
| L15<br>SEQ ID No. 16 | TTGTGGCTACAATGTGCTAG |

Sequences of Oligonucleotides used for PCR and sequencing primers and hybridization probes. The locations of the template regions corresponding to the primers are shown in FIG. 3. LPV oligos were used to construct the pLPc mutagenesis vector, and the LPH oligos were used to construct the pLPeΔsunA plasmid, which was used to construct B. subtilis LPeΔsunA. LPVF and LPHF oligos prime in the forward direction, and the LPVR and LPHR oligos prime in the reverse direction. Oligonucleotide L13 was used as a sequencing primer that was about 220 nt upstream of the sublancin gene, and L15 was used as a hybridization probe within the sublancin gene.

A. Construction of pLPVc Vector by PCR Cloning.

The primary vector, pLPVc, was constructed from components synthesized by PCR and assembled in the EcoRI-HindIII site of the *E. coli* plasmid pTZ. The complete assembled EcoRI-HindIII insert sequence of pLPVc is shown in FIG. 4. This insert contains a 650 base pair upstream chromosomal homology, followed by a cat gene that has been inserted into an engineered BamHI site, followed by the presublancin (sunA) gene, which contains a translationally-silent XhoI site in the leader region of SunA, and the natural PstI site in the C-terminal region, which is followed by a 650 by of downstream chromosomal homology. This plasmid constitutes a cassette-mutagenesis system, in which the sequence of the mature region of SunA can be modified by replacing the XhoI-PstI fragment with a mutagenized sequence.

B. Construction of the *B. subtilis* LPeΔsunA Host.

The pLPVc plasmid was then modified in order to construct pLPHe, which was used to engineer a deletion in the chromosomal sunA gene and replace the cat gene with an erm gene. The pLPHe plasmid, shown in FIG. 5, contains an erm gene in the BamHI site, and 47 codons are removed from the central region of the 56-codon sunA ORF. The remaining 9 codons are in-frame in order to minimize any effects of the deletion on the expression of downstream genes that may be required for sublancin biosynthesis. This in-frame construction was to permit this host to be used for expression of sublancin genes in trans, from a plasmid, as well as by integration into the chromosome.

The use of these plasmids in making sublancin mutants is diagrammed in FIG. 4. First, a double-recombination between pLPHe and the *B. subtilis* 168 chromosome replaces the sunA gene with an erm gene. The resulting *B. subtilis* LPeΔsunA is erythromycin resistant and does not produce sublancin. The pLPVc plasmid was then used to introduce a mutagenized copy of sunA, at precisely the same location occupied by the original sunA gene by means of a double-recombination that replaces the erm gene and sunA deletion with a cat gene and the mutant sunA' gene. The cat gene is placed upstream from the sunA' promoter so as to not interfere with expression of the sunA' gene.

A halo assay was used to compare the amount of antibiotic production by *B. subtilis* 168 with that of the LPeΔsunA deletion strain. The amount of antibiotic activity produced by a bacterial colony was determined by its ability to inhibit outgrowth of *Bacillus cereus* T spores to produce a halo around the colony. *B. cereus* T spores were prepared by suspending 250 mg of lyophilized spores (11), in 30 ml of sterile water and subjecting them to heat shock for 2 hr at 65° C. The spores were centrifuged and resuspended in 50 ml of 10% ethanol. This solution was used to spray Medium A plates on which colonies had grown to a diameter of 1 mm. The plates were incubated 5 to 12 hr to allow the spores to germinate and outgrow. The diameters of the clear halos were used to compare the amount of antibiotic produced by the colonies.

Figure 6:
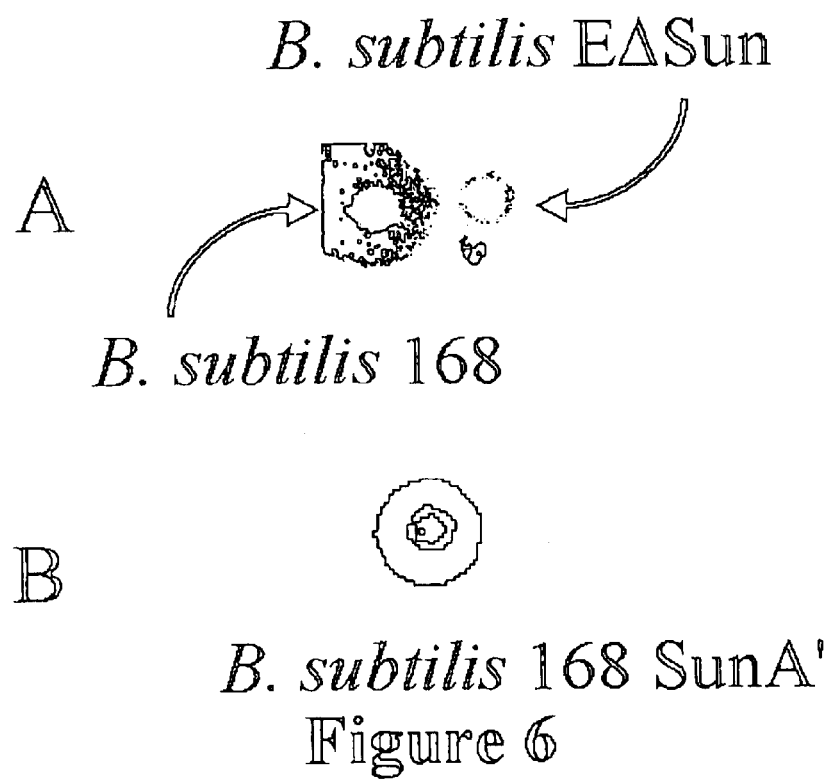
FIG. 6. Lack of sublancin production in *B. subtilis* EΔSun, and its restoration by integration of the sunA' gene. Panel A. Halo assay showing sublancin production from wild-type *B. subtilis* 168, compared to the EΔSun deletion strain. Panel B. Halo assay showing production of sublancin after restoration of the sublancin gene as sunA', which has translationally-silent mutations.

As shown in FIG. 6, the difference is dramatic, with the wild-type strain giving a large halo, and the deletion strain a barely detectable one. Under these growth conditions, sublancin constitutes a large majority of the antimicrobial activity produced by *B. subtilis* 168.

C. Integration of the sunA' Gene Restores Sublancin Biosynthesis.

The sublancin gene subcloned into the plasmid pLPVc is sunA', which is identical to sunA except for the translationally-silent mutations used to create the XhoI site. Since sunA encodes the same amino acid sequence as the natural sunA gene, placing sunA' into the chromosome at the location originally occupied by sunA would be expected to restore sublancin production. FIG. 6 shows a halo assay demonstrating that recombinant cells having the sunA' gene integrated into the chromosome are restored in their expression of antimicrobial activity.

The molecular mass of sublancin was determined using electrospray ionization mass spectroscopy (ESI-MS) on a single quadropole ion-trap mass spectrometer in positive ion mode (LCQ, Finnigan, San Jose, Calif.). The source conditions were as follows: sheath gas flow, 40 units, ESI spray voltage, 5 kV, capillary temperature 200° C., capillary voltage 46 V. MS data were acquired on a Windows NT worksation running the LCQExplore software package (Finnigan). MALDI-TOF MS were carried out in positive-ion mode (Proflex, Bruker, Manning Park, Mass.). Sinapinic acid, dissolved in acetonitrile, 0.1% TFA (3:7), was used as matrix. The sample and matrix were applied to the sample target (Bruker) according to the sandwich method of Kussman et al. (12). Tryptic digest fragments were sequenced using tandem MS/MS, using the nanospray adapter on the Finnigan LCQ (nanoESI-MS/MS). Nanospray capillaries (Protana, Odense, Denmark) were used to supply the sample to the LCQ at a very low flow rate (1–10 nl/min). The source conditions were as follows: ESI spray voltage, 0.8–0.1 kV, capillary temperature 200° C., capillary voltage 41 V, MS/MS relative collision energy, 80%. Sequence interpretation was assisted by the use of AminoCalc software (Protana).

The active peak emerged from the HPLC column at the same gradient position as natural sublancin (data not shown), and mass spectral analysis using MALDI-TOF gave a major species with a molecular mass of 3881 Da. The molecular weight species corresponded to the 3881 Da positive control using natural sublancin. This molecular weight is also very close to the 3878 molecular weight previously reported for sublancin (6). These results demonstrate that B. subtilis LPeΔsunA host has been stably converted to express sublancin by the pLPVc plasmid, and that the presence of the cat gene upstream from the sunA gene does not interfere with sunA expression.

EXAMPLE 2

Construction and Expression of a Soluble Sublancin Structural Mutant

The pLPVc plasmid was tested for its utility in the construction and expression of mutant sublancin peptides. One mutant was Dha16T, in which the Dha residue was replaced with a threonine. The ability to generate the Dha16T mutant addressed the question as to whether the sublancin processing machinery is sufficiently flexible in its recognition and processing of the presublancin peptide to convert a threonine residue at position 16, which is normally a serine, to the corresponding Dhb residue. The success in obtaining the mutant demonstrates that the sublancin processing machinery is relatively tolerant of structural changes in its substrate. These results are strongly indicative of the ability of sublancin biosynthesis pathway to process precursors with a variety of other changes. These positive results also provide the basis on which to conduct a comprehensive structure-function analysis of sublancin.

This plasmid construct was also tested for its biological activity toward inhibition of bacterial outgrowth, and found to be active. Mass spectral analysis showed that the molecular weight of the Dha16T mutant is exactly as expected for the threonine having undergone dehydration. This demonstrates that the threonine had been correctly processed to a Dhb residue, and that the sublancin processing machinery is capable of correctly recognizing and processing a residue that is not normally a component of the sublancin molecule.

EXAMPLE 3

Figure 5:
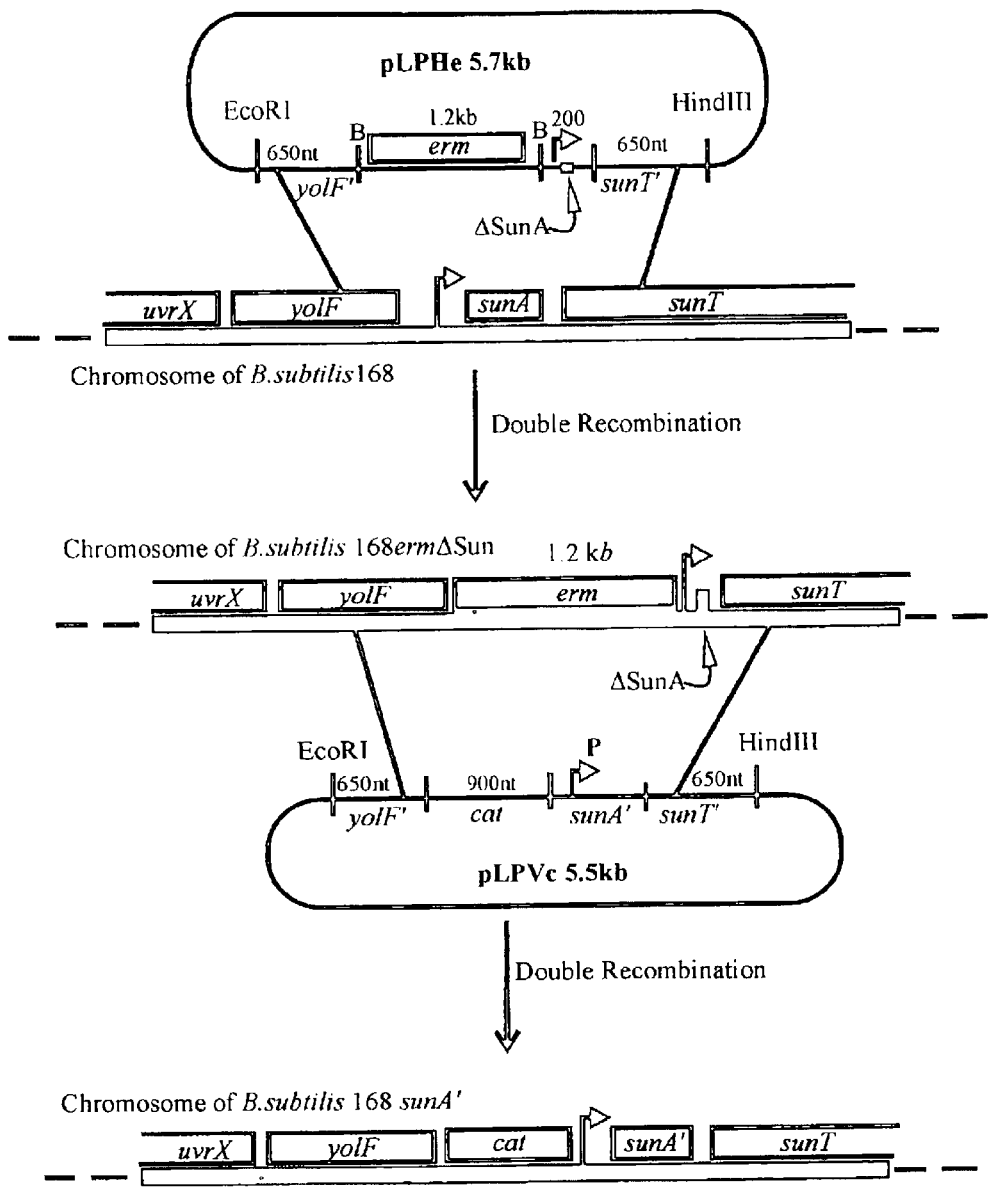
FIG. 5. Strategy for the construction of the host-vector pair used to make sublancin mutants. Plasmid pLPHerm was linearized and transformed into wild-type *B. subtilis* 168. Double recombinants in which the SunA ORF was replaced by an erm gene and the ΔsunA ORF were selected on erythromycin plates. These mutants, which are erythromycin resistant and encode a defective SunA, peptide, were characterized as shown in FIG. 5. One of the mutants was selected and designated as *B. subtilis* LPeΔsunA.

Construction of the Display Peptide Consisting of the Sublancin Prepeptide with a 20-Residue Polyglycine and the Subtilin Leader Segment at the C-Terminus of the Prepeptide FIG. 2 shows the basic design of the display peptide. The actual sequence that was constructed is shown in FIG. 7. As outlined in FIG. 2, this peptide consists of the sublancin precursor peptide (which contains the sublancin leader and the sublancin mature segment), fused at its C-terminus to a glycine residue spacer, followed by the subtilin leader segment. This sequence was constructed in the pLPcat vector shown in FIG. 5, and transformed into the chromosome of the B. subtilis 168 ermΔSun host, as shown in FIG. 5.

EXAMPLE 4

Expression of the Lantibody Display Peptide

Figure 8:
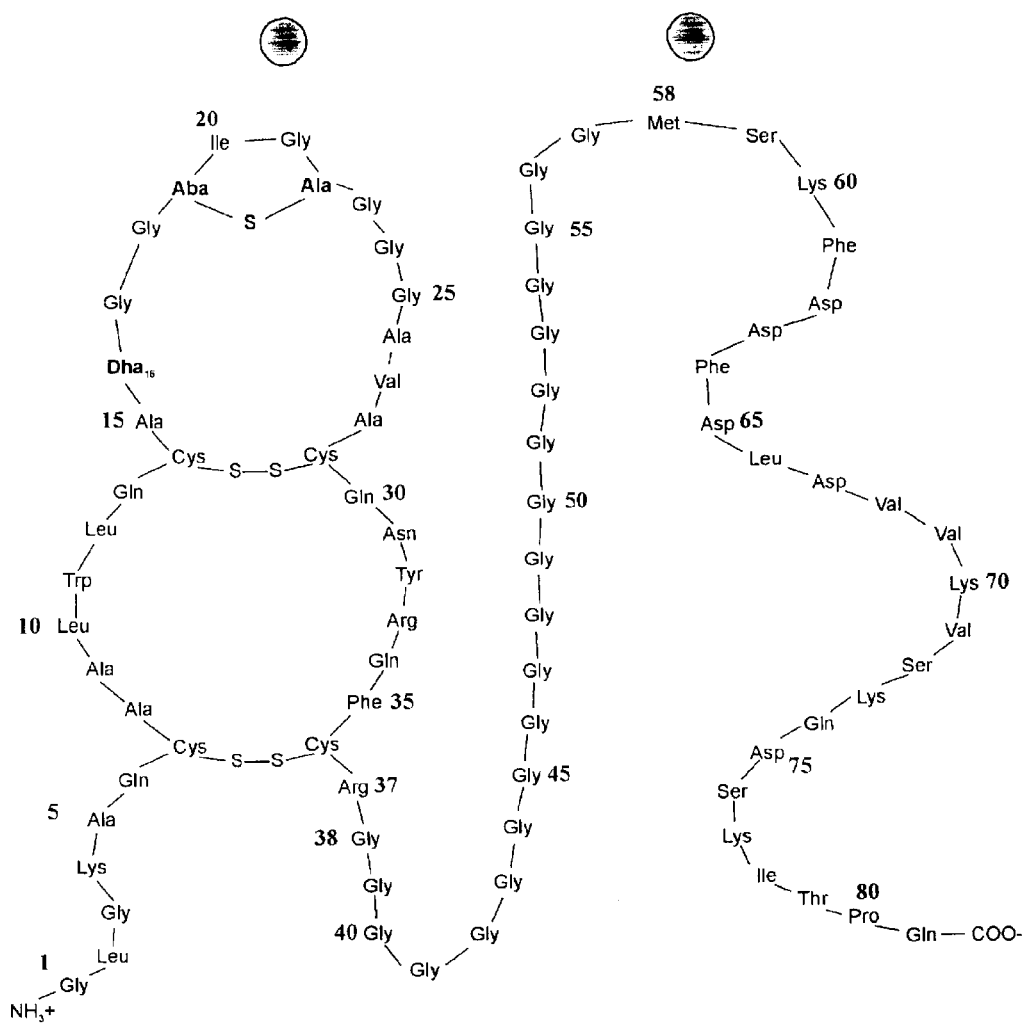
FIG. 8. Lantibody Display Peptide as expressed from *B. subtilis* 168 consists of mature sublancin segment (1–37), a 20-residue polyglycine spacer (38–57) and the subtilin leader segment (58–81) (SEQ ID No. 2).

The transformed host was cultured in Medium A to allow the Lantibody Display Peptide to be expressed. Expression was monitored by observing the appearance of the Display Peptide in the cytoplasm of the cell, the membrane, the cell wall and in the extracellular medium. The peptide was detected using polyclonal antibodies raised in rabbits against a sublancin-KLH conjugate as an antigen. Solubilized components from the different cell fractions were applied to a reversed-phase HPLC column (4), and the fractions were analyzed using mass spectroscopy. One of the most important observations was that the cell wall contained considerable amounts of a species with a molecular-weight corresponding to the full-length peptide as shown in FIG. 8. Moreover, none of this full-length peptide appeared in the extracellular fluid, showing that it is tenaciously bound to the cell wall as was predicted from the ability of the subtilin leader segment to bind to the cell wall (13). However, several degradation products of the full-length peptide did appear. Several extracellular components corresponded to products resulting from cleavage within the polyglycine spacer, and several others which corresponded to products resulting from cleavage within the subtilin leader segment. Of particular interest was an extracellular species with a molecular weight corresponding to amino acid residues 1–77, which would result if 4 residues were cleaved from the C-terminal end. The fact that this peptide was released into the culture supernatant whereas the full length (1–81) peptide was not, shows that the tetrapeptide sequence at the C-terminal end is crucial to provide the tight binding to the cell wall. Those peptides released into the medium had antimicrobial activity, showing that the C-terminal modification of sublancin does not disrupt the posttranslational modification process. Those results also demonstrate the ability of the sublancin Display Peptide to recognize and bind to a target substrate, i.e., the polyclonal antibody, and that this activity is not lost as a result of the structural modifications to the protein.

EXAMPLE 5

The Location of the Lantibody Display Peptide in the Cell Wall is Near the Surface In order to fulfill the concept of the Lantibody Display Library, it is necessary that the Lantibody Display Peptide be located near the surface of the cell where it can interact with ligands so that the screening procedures, as outlined above, can be carried out. To explore this hypothesis, cells expressing the Lantibody Display Peptide as shown in FIG. 8 were centrifuged out of the culture medium and resuspended in buffer. The cell suspension was treated with anti-sublancin antibodies, and washed to remove any unbound antibody. To determine whether anti-sublancin antibodies were bound to the surface of the cells, goat anti-rabbit antibodies that were conjugated with horseradish peroxidase were added and allowed to adsorb to any antibodies on the surface of the cells. The cells were washed and the peroxidase color reagent was added. The cells quickly became intensely blue, showing that rabbit antibodies were present. Control cells that lacked the sublancin gene were colorless, showing that the color was indeed because of the presence of sublancin within the cell-wall matrix. These results demonstrate that the location of the sublancin within the cell wall is accessible to antibodies that have diffused into the matrix. Under the transfection conditions, the Sublancin Display Peptide is the primary species of protein in the cell wall fraction, so the Sublancin Display Peptide is responsible for the binding to sublancin antibodies.

To determine whether the sublancin is embedded deeply within the cell-wall matrix or near or on the surface, experiments were conducted using magnetic beads that were coated with anti-rabbit antibodies (beads obtained from Dynal, Inc.). These beads were added to a suspension of Sublancin Display Peptide-producing cells that had been treated with anti-sublancin antibodies, and thoroughly washed. After incubating for 16 hr, microscopic examination showed that the cells had aggregated onto the surface of the beads, indicating that the cells were coated with rabbit antibodies that could interact with the anti-rabbit antibodies on the beads. Cells that did not contain a gene for sublancin did not show such aggregations, which establishes that the interaction between cells and beads is a result of the presence of the Sublancin Display Peptide very near to or on the surface of the cells.

REFERENCE LIST

1. Hansen, J. Norman. 1997. "Nisin and Related Antimicrobial Peptides", In Biotechnology of Anitbiotics, ed. Wm. R. Strohl, pp. 437–467.

2. Davies, D. R. and H. Metzger. 1983. Structural basis of antibody function. Annu Rev Immunol 1: 87–117.

3. Moller, G. 1973. Lymphocyte immunoglobulin: Synthesis and surface representation. Transplantation Reviews 14.

4. Paik, S. H., A. Chakicherla, and J. N. Hansen. 1998. Identification and characterization of the structural and transporter genes for, and the chemical and biological properties of, sublancin 168, a novel lantibiotic produced by Bacillus subtilis 168. J Biol Chem 273: 23134–23142.

5. Kunst, F., N. Ogasawara, I. Moszer, A. M. Albertini, G. Alloni, V. Azevedo, M. G. Bertero, P. Bessieres, A. Bolotin, S. Borchert, R. Borriss, L. Boursier, A. Brans, M. Braun, S. C. Brignell, S. Bron, S. Brouillet, C. V. Bruschi, B. Caldwell, V. Capuano, N. M. Carter, S. K. Choi, J. J. Codani, I. F. Connerton, A. Danchin, and et al. 1997. The complete genome sequence of the gram-positive bacterium Bacillus subtilis. Nature 390: 249–256.

6. Sanger, F., S. Nicklen, and A. R. Coulson. 1977. DNA sequencing with chain-termination inhibitors. Proc. Natl. Acad. Sci. USA 74: 5463–5467.

7. Paul, L. K., G. Izaguirre, and J. N. Hansen. 1999. Studies of the subtilin leader peptide as a translocation signal in Escherichia coli K12. FEMS Microbiol Lett 176: 45–50.

8. Banerjee, S. and J. N. Hansen. 1988. Structure and expression of a gene encoding the precursor of subtilin, a small protein antibiotic. Journal of Biological Chemistry 263: 9508–9514.

9. Liu, W. and J. N. Hansen. 1992. Enhancement of the chemical and antimicrobial properties of subtilin by site directed mutagenesis. Journal of Biological Chemistry 267: 25078–25085.

10. Young, F. E. and G. A. Wilson. 1974. Bacillus subtilis, p.69–114. In R. C. King (ed.), Handbook of Genetics. Plenum Press, New York.

11. Vary, J. C. and H. O. Halvorson. 1965. Kinetics of germination of Bacillus spores. J. Bacteriol. 89: 1340–1347.

12. Kussman, M., E. Nordhoff, H. Rahbek-Nielsen, S. Haebel, M. Rossel-Larsen, L. Jakobsen, J. Gobom, E. Mirgorod-Skaya, A. Kroll-Kristensen, L. Palm, and P. Roepstorff. June, 1997. Matrix-assisted laser desorption/ionization mass spectrometry sample preparation techniques designed for various peptide and protein analytes. J. Mass spectrum. 32: 593–601.

13. Paul, L. K., G. Izaguirre, and J. N. Hansen. 1999. Studies of the subtilin leader peptide as a translocation signal in Escherichia coli K12. FEMS Microbiol Lett 176: 45–50.

What is claimed:

1. A Lantibiotic Display Peptide comprising a chimeric polypeptide comprising a lantibiotic peptide, an amino acid spacer attached to the C-terminus of the lantibiotic peptide, and a subtilin leader segment attached to the spacer comprising amino acid residues selected from the group consisting of residues 58–81 of SEQ ID No. 2, residues 68–81 of SEQ ID No. 2, and residues 78–81 of SEQ ID No. 2, and wherein the lantibiotic peptide is sublancin 168 comprising amino acid residues 1–38 of SEQ ID No. 2.

2. The Lantibiotic Display Peptide of claim 1, wherein the lantibiotic peptide is obtained from *Bacillus subtilis*.

3. The Lantibiotic Display Peptide of claim 2, wherein the lantibiotic peptide is obtained from *Bacillus subtilis* strain 168.

4. The Lantibiotic Display Peptide of claim 1 wherein the spacer comprises from 15–25 amino acid residues.

5. The Lantibiotic Display Peptide of claim 1, wherein the spacer comprises about 20 amino acid residues.

6. The Lantibiotic Display Peptide of claim 1, wherein the subtilin leader segment comprises amino acid residues 58–81 of SEQ ID No. 2.

7. The Lantibiotic Display Peptide of claim 1, wherein the subtilin leader segment comprises amino acid residues 68–81 of SEQ ID No. 2.

8. The Lantibiotic Display Peptide of claim 1, wherein the subtilin leader segment comprises amino acid residues 78–81 of SEQ ID No. 2.

* * * * *

SEQUENCE LISTING

```
<160> NUMBER OF SEQ ID NOS: 3

<210> SEQ ID NO 1
<211> LENGTH: 2517
<212> TYPE: DNA
<213> ORGANISM: Artificial Sequence
<220> FEATURE:
<223> OTHER INFORMATION: The EcoRI-HindIII insert of the pLPVc
      integrative plasmid.

<400> SEQUENCE: 1
gaattccggc tctaaagcga ttctgagagc agtttcttat acaccagcag gaactgcact      60
tcaacgagct ggattaacag gtgggcataa gagttaagat aaatttaaac ttatataaca     120
catcgcttaa agttttttg ttttaaaaac ttaaaaaaca tggtaaaatt atataaaaac     180
ataagaaaga gtgattatat ggaatatgta gttatgataa tcattttatt agcacttttc     240 tttatttta ctgttttcct aaatacacgt tatagttttg atgaaaaatg cttagtctta     300
```

-continued

```
aaatttggtt tatctaaaac agaaattcca attaatcaaa tagttagtat taaagagtca    360
gacaagtatg gagttgcaga taatatcgat tataaaattg gtatgccata tgctcaacca    420
gatagaattg ttattgaaac tacaaataag cgttttctag tttttttaaa tggagctcaa    480
caatttattc aaaagtataa aagggttagt gtttgaacat aaaaaagtac cttcttacaa    540
tagaaggtac tttttgtat ctataattat taaaaattta cctaaatttt tatcattatt     600
aattcaaaat aaatccataa tagtcaattt tatttagtgt attacaacca attcggatcc    660
aagcacccat tagttcaaca aacgaaaatt ggataaagtg ggatatttt aaaatatata     720
tttatgttac agtaatattg acttttaaaa aaggattgat tctaatgaag aaagcagaca    780
agtaagcctc ctaaattcac tttagataaa aatttaggag gcatatcaaa tgaactttaa    840
taaaattgat ttagacaatt ggaagagaaa agagatattt aatcattatt tgaaccaaca    900
aacgactttt agtataacca cagaaattga tattagtgtt ttataccgaa acataaaaca    960
agaaggatat aaattttacc ctgcatttat tttcttagtg acaagggtga taaactcaaa   1020
tacagctttt agaactggtt acaatagcga cggagagtta ggttattggg ataagttaga   1080
gccactttat acaattttg atggtgtatc taaaacattc tctggtattt ggactcctgt    1140
aaagaatgac ttcaaagagt tttatgattt ataccttct gatgtagaga aatataatgg    1200
ttcggggaaa ttgtttccca aaacacctat acctgaaaat gcttttctc tttctattat    1260
tccatggact tcatttactg ggtttaactt aaatatcaat aataatagta attaccttct   1320
acccattatt acagcaggaa aattcattaa taaaggtaat tcaatatatt taccgctatc   1380
tttacaggta catcattctg tttgtgatgg ttatcatgca ggattgttta tgaactctat   1440
tcaggaattg tcagataggc ctaatgactg gcttttataa tatgagataa tgccgactgt   1500
acttttaca gtcggttttc taatgtcact aacctgcccc gttagttgaa gaagggattc     1560
gtgtattaca accaattctg tttattgata ggtaataaag ttttttttct atgatttatg   1620
aacaagtttc cttataattt tcaaaaaaaa ataaaaaata tggttgaatt tagatttatc   1680
ttcctttata ttaaaaaatg taatccggat tgcaaacaaa tggggaggtt ttacaaatgg   1740
aaaagctatt taaagaagtt aaactcgagg aactcgaaaa ccaaaaaggt agtggattag   1800
gaaaagctca gtgtgctgcg ttgtggctac aatgtgctag tggcggtaca attggttgtg   1860
gtggcggagc tgttgcttgt caaaactatc gtcaattctg cagataaaac atttgtagag   1920
ggaatatttt aaatattccc tcatatttaa agcggggatt gaaattgaat aagaaaaaga   1980
aatatgttca tactaaacag tttaatagtc atgattgtgg actagcttgt atctcgtcaa   2040
ttttaaagtt tcataacctt aactatgaaa ttgatttctt actagaccta attggggata   2100
aggaaggcta tagtttaaga gacttaattg ttatttttaa gaagatgggg ataaaaacta   2160
ggccacttga attgcaagaa aataagacat tcgaagccct aaaacaaata aagctcccctt   2220
gtatagcttt gttagaaggg gaggaatatg gacattacat aacaatatac gaaattagaa    2280
ataactattt acttgttagt gatcctgata agacaaaat aactaaaata aaaaagagg      2340
attttgaaag taaattcaca aactttatat tagaaattga caaagagtca attcctgaaa    2400
aagaaaaaga tcaaaaaaaa cattcttact ttttaaagga catacttttt agaaataaat    2460
tgatcgtttt tgtgattta ttgacttcct tgttcgttgt gggtcttgct gaagctt        2517
```

<210> SEQ ID NO 2
<211> LENGTH: 300
<212> TYPE: DNA
<213> ORGANISM: Artificial Sequence

```
<220> FEATURE:
<223> OTHER INFORMATION: The sequence of sunA-PG20-SL gene and
      corresponding peptide sequence.
<221> NAME/KEY: CDS
<222> LOCATION: (1)..(300)
<223> OTHER INFORMATION:

<400> SEQUENCE: 2 atg gaa aag cta ttt aaa gaa gtt aaa ctc gag gaa ctc gaa aac caa        48
Met Glu Lys Leu Phe Lys Glu Val Lys Leu Glu Glu Leu Glu Asn Gln
1               5                   10                  15 aaa ggt agt gga tta gga aaa gct cag tgt gct gcg ttg tgg cta caa        96
Lys Gly Ser Gly Leu Gly Lys Ala Gln Cys Ala Ala Leu Trp Leu Gln
                20                  25                  30 tgt gct agt ggc ggt aca att ggt tgt ggt ggc ggc gcc gtt gct tgt       144
Cys Ala Ser Gly Gly Thr Ile Gly Cys Gly Gly Gly Ala Val Ala Cys
            35                  40                  45 caa aac tat cgt caa ttc tgt aga ggt ggt ggt ggg gga ggc ggg gga       192
Gln Asn Tyr Arg Gln Phe Cys Arg Gly Gly Gly Gly Gly Gly Gly Gly
        50                  55                  60 ggg ggt ggt ggt gga gga ggt ggt ggt ggt ggt atg tca aag ttc           240
Gly Gly Gly Gly Gly Gly Gly Gly Gly Gly Gly Met Ser Lys Phe
65                  70                  75                  80 gat gat ttc gat cta gat gtt gtg aaa gtc tct aaa caa gac tca aaa       288
Asp Asp Phe Asp Leu Asp Val Val Lys Val Ser Lys Gln Asp Ser Lys
                85                  90                  95 atc act ccg caa                                                       300
Ile Thr Pro Gln
            100

<210> SEQ ID NO 3
<211> LENGTH: 100
<212> TYPE: PRT
<213> ORGANISM: Artificial Sequence
<220> FEATURE:
<223> OTHER INFORMATION: The peptide sequence of sunA-PG20-SL.

<400> SEQUENCE: 3

Met Glu Lys Leu Phe Lys Glu Val Lys Leu Glu Glu Leu Glu Asn Gln
1               5                   10                  15

Lys Gly Ser Gly Leu Gly Lys Ala Gln Cys Ala Ala Leu Trp Leu Gln
                20                  25                  30

Cys Ala Ser Gly Gly Thr Ile Gly Cys Gly Gly Gly Ala Val Ala Cys
            35                  40                  45

Gln Asn Tyr Arg Gln Phe Cys Arg Gly Gly Gly Gly Gly Gly Gly Gly
        50                  55                  60

Gly Gly Gly Gly Gly Gly Gly Gly Gly Gly Met Ser Lys Phe
65                  70                  75                  80

Asp Asp Phe Asp Leu Asp Val Val Lys Val Ser Lys Gln Asp Ser Lys
                85                  90                  95

Ile Thr Pro Gln
            100
```